United States Patent [19]
Patel

[11] Patent Number: 6,084,103
[45] Date of Patent: Jul. 4, 2000

[54] ONE POT SYNTHESIS OF 2-OXAZOLIDINONE DERIVATIVES

[75] Inventor: Rajnikant Patel, Dartford, United Kingdom

[73] Assignee: Zeneca Limited, London, United Kingdom

[21] Appl. No.: 09/011,045

[22] PCT Filed: Aug. 2, 1996

[86] PCT No.: PCT/GB96/01885

§ 371 Date: May 13, 1998

§ 102(e) Date: May 13, 1998

[87] PCT Pub. No.: WO97/06162

PCT Pub. Date: Feb. 20, 1997

[30] Foreign Application Priority Data

Aug. 7, 1995 [GB] United Kingdom ............... 9516145

[51] Int. Cl.[7] ...................... C07D 263/04; C07D 263/16
[52] U.S. Cl. ............................................. 548/229
[58] Field of Search ................................. 548/229

[56] References Cited

U.S. PATENT DOCUMENTS 5,399,574  3/1995  Robertson et al. ................. 514/339
5,466,699  11/1995  Robertson et al. ................. 514/323

FOREIGN PATENT DOCUMENTS 0313 397   4/1989   European Pat. Off. .
91/18897  12/1991   WIPO .
95/20588   8/1995   WIPO .

Primary Examiner—Mukund J. Shah
Assistant Examiner—Tamthom N. Truong
Attorney, Agent, or Firm—Finnegan, Henderson, Farabow, Garrett & Dunner, L.L.P.

[57] ABSTRACT

The present invention provides an improved process for preparing (S)-4-{[3-[2-(dimethylamino)ethyl]-1H-indol-5-yl]methyl}-2-oxazolidinone which comprises: a) forming a carbamate of formula (III), from methyl 4-nitro-(L)-phenylalaninate hydrochloride; b) reducing the compound of formula (III) to give the compound of formula (IV); c) reducing the methyl ester grouping in the compound of formula (IV) to give the compound of formula (V); d) ring closure of the compound of formula (V) to give the compound of formula (VI); e) diazonium salt formation from the compound of formula (VI) followed by reduction to give the compound of formula (VII); f) Fischer reaction of the compound of formula (VII) to give (S)-4-{[3-[2-(dimethylamino)ethyl]-1H-indol-5-yl]methyl}-2-oxazolidinone.

20 Claims, No Drawings

ONE POT SYNTHESIS OF 2-OXAZOLIDINONE DERIVATIVES

This is a 371 application of PCT/GB96/01885 filed Aug. 2, 1996.

The present invention relates to an improved process for preparing substituted indole derivatives which are useful for the treatment and prophylaxis of migraine. More particularly, the present invention provides an improved process for the preparation of the $5HT_1$-like receptor agonist (S)-4-{[3-[2-(dimethylamino)ethyl]-1H-indol-5-yl]methyl}-2-oxazolidinone, which is known to be effective for the treatment of migralne.

Selective $5$-$HT_1$-like receptor agonists are known to be useful therapeutic agents. The $5$-$HT_1$-like receptor mediates vasoconstriction and thus modifies blood flow in the carotid vascular bed. European patent specification 0313397 describes a class of specific $5$-$HT_1$-like receptor agonists which are beneficial in the treatment or prophylaxis of conditions wherein vasoconstriction in the carotid vascular bed is indicated, for example, migraine, a condition associated with excessive dilation of the carotid vasculature.

International patent specification WO91/18897 describes a further class of compounds having exceptional "5-HT1-like" receptor agonism and excellent absorption following oral dosing. These properties render the compounds disclosed in WO91/18897 particularly useful for certain medical applications, notably the prophylaxis and treatment of migraine, cluster headache and headache associated with vascular disorders, hereinafter referred to collectively as "migraine". One particularly preferred compound described in WO91/18897 is (S)-N,N-dimethyl-2-[5-2oxo-1,3-oxazolidin-4-yl-methyl)-1H-indol-3-yl]ethylamine which is also known as (S)-4-{[3-[2-(dimethylamino)ethyl]-1H-indol-5-yl]methyl}-2-oxazolidinone and can be represented by formula (I):

The compound of formula (I) can exist as its (S) or (R) enantiomer and is specifically exemplified in WO91/18897. A number of possible routes for preparing the compound of formula (I) are suggested in WO91/18897.

A new process for preparing the compound of formula (I) has now been discovered. This process is advantageous over the processes disclosed in WO91/18897 in that it allows the final product to be made at a high yield on a large scale and in pure form by using a one pot procedure, thus avoiding the need for time-consuming and costly isolation of intermediates. The new process also avoids the need for dangerous reagents such as phosgene or environmentally hazardous reagents such as tin chloride.

According to the first aspect of the present invention, therefore, there is provided a process for the preparation of a (S)-4-{[3-[2(dimethylamino)ethyl]-1H-indol-5-yl]methyl}-2-oxazolidinone which process comprises the steps of a) forming a carbamate from methyl 4-nitro-(L)-phenylalaninate hydrochloride, represented by formula (II)

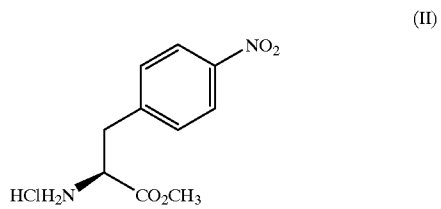

by adding sodium carbonate or sodium hydrogen carbonate and n-butyl chloroformate and reacting to give methyl(S)-N-butoxycarbonyl4-nitrophenylalaninate, represented by formula (III)

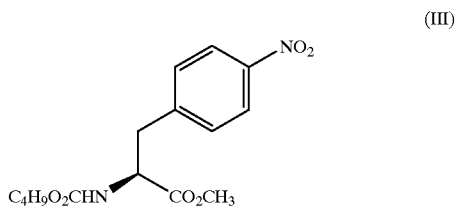

b) reducing the compound of formula (III) to give methyl (S)-N-butoxycarbonyl4-amino phenylalaninate, represented by formula (IV)

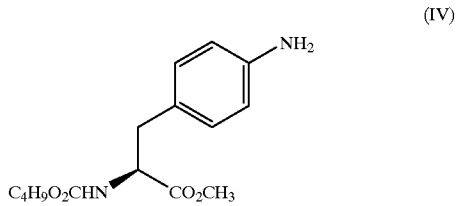

c) reducing the methyl ester grouping —$CO_2CH_3$ in the compound of formula (IV) to give (S)-N-butoxycarbonyl-4-aminophenylalaninol, represented by formula (V)

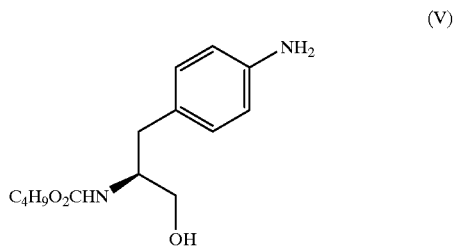

d) a ring closure of the compound of formula (V) to give (S)-4-(4-aminobenzyl)-2-oxazolidinone, represented by formula (VI)

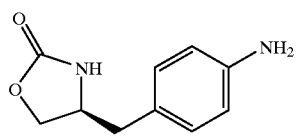

e) preparation of the diazonium salt of the compound of formula (VI) followed by reduction to give the hydrazine (S)-4-4-hydrazinobenzyl)-2-oxazolidinone hydrochloride, represented by formula (VII)

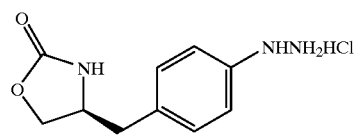

f) Fischer reaction of the compound of formula (VII) to give the compound of formula (I)

Suitably, one or more of steps a) to f) are carried out using a one pot procedure. Preferably steps a) to d) are carried out by a one pot procedure followed by isolation of the compound of formula (VI) and then a second one pot procedure for steps e) and f).

Step a) is conveniently carried out in the presence of a solvent e.g. aqueous ethyl acetate or dioxane. Aqueous ethyl acetate is preferred. Sodium carbonate is used in preference to sodium hydrogen carbonate and is preferably added prior to the n-butyl chloroformate. The reaction is conveniently carried out at a non-extreme temperature, suitably in the range 5–60° C. Preferably the reaction is carried out at 15–35° C. In a particularly preferred embodiment the addition of sodium carbonate takes place at a temperature of approximately 20° C. and the addition of N-butyl chloroformate takes place at a temperature of approximately 30° C.

The reduction step b) is conveniently carried out in the presence of an organic solvent, e.g. ethyl acetate or ethanol. Preferably step b) is carried out by a one pot procedure using the ethyl acetate solution of the compound of formula (III) which results from step a). Suitably, step b) is carried out by hydrogenation, preferably in the presence of a catalyst such as palladium charcoal. The reaction may be carried out under an atmosphere of nitrogen using hydrogen at normal atmospheric pressure at room temperature. Hydrogenation is preferably carried out at approximately 20 psi of hydrogen at an elevated temperature e.g. 30° C. to 50° C. The resulting ethyl acetate solution of the compound of formula (IV) is preferably converted into a butanol solution which can be used directly, as part of a one pot procedure, in step c). This conversion can conveniently be carried out by partial distillation of the ethyl acetate solution followed by addition of butanol and fractionation to remove the ethyl acetate.

The methyl ester reduction of step c) is conveniently carried out in the presence of a solvent e.g. SVM or n-butanol. Preferably step c) is carried out as part of a one pot procedure by preparing a n-butanol solution from the ethyl-acetate solution of the compound of formula (IV) and then directly reducing the n-butanol solution. The reduction is preferably effected using sodium borohydride and is conveniently carried out at a non-extreme temperature suitably 20–40° C. Preferably, the reduction is carried out in two phases; the first phase being carried out under nitrogen at a temperature of approximately 25° C; and the second phase being carried out at approximately 30° C. The resulting n-butanol solution of the compound of formula (V) can then be dried using hydrochloric acid and ammonia. The dry n-butanol solution can be used directly in step d) as part of a one pot procedure.

Step d) is preferably carried out on a dry solution, e.g. a dry butanol solution, of the compound of formula (V). Such a dry butanol solution is advantageously prepared by drying the n-butanol solution which is produced by step c). The dry n-butanol solution is preferably decolourised using charcoal before carrying out the ring closure reaction. The ring closure can be conveniently effected using sodium methoxide, suitably in an alcoholic solvent e.g. methanol. Most preferably, the ring closure is carried out using a 30% solution of sodium methoxide in methanol. The reaction is preferably carried out at an elevated temperature which is suitably in the range 50–120° C. Preferably the reaction is carried out at approximately 85° C. The resulting compound of formula (VI) may then be isolated. This isolation can be carried out by standard centrifugation, filtration and drying methods.

Step e) is preferably carried out on the isolated compound of formula (VI). Isolation can be achieved, for example, using well known centrifugation, filtration and drying techniques. Diazonium salt formation can be carried out using aqueous sodium nitrite solution, preferably in the presence of concentrated hydrochloric acid, at a reduced temperature. Preferably the salt formation is carried out at a reduced temperature, e.g. 0–5° C. Hydrazine formation is then carried out on the diazonium salt solution by using sodium sulphite as a reducing agent. The sodium sulphite is suitably in the form of an aqueous solution. The reduction is advantageously carried out in two phases: the first being addition of sodium sulphite; the second being addition of hydrochloric acid. Preferably the first phase is carried out at a temperature below 10° C. The second phase is preferably carried out at an elevated temperature e.g. 55–60° C.

The solution of the compound of formula (VII) which results from step e) is preferably used directly in step f) as a one pot procedure. Step f) is a Fischer reaction. It has been found to be advantageous to carry out this reaction at a relatively high dilution in order to maximise the purity of the final product. Accordingly the solution which results from step e) is preferably diluted with water. The Fischer reaction is then carried out by adding 4,4-diethoxy-N,N-dimethylbutylamine, suitably under a nitrogen atmosphere. Preferably, when the 4,4-diethoxy-N,N-dimethylbutylarnine is added, the diluted solution is at an elevated temperature. A suitable temperature is in the range 75–105° C., and is preferably approximately 90° C. The reaction preferably proceeds under reflux.

When the reaction is complete, the compound of formula (I) can be extracted using standard techniques. Suitably the refluxed reaction product is cooled and adjusted to about pH7, e.g. using sodium hydroxide. The pH adjusted product can then be extracted with ethyl acetate and the aqueous layer adjusted to about pH 10 with sodium hydroxide. The product can then be extracted at approximately 50° C., followed by standard decolourising, filtration, distillation, centrifugation and drying techniques.

A particularly preferred reaction scheme for the preparation of the compound of formula (I) is

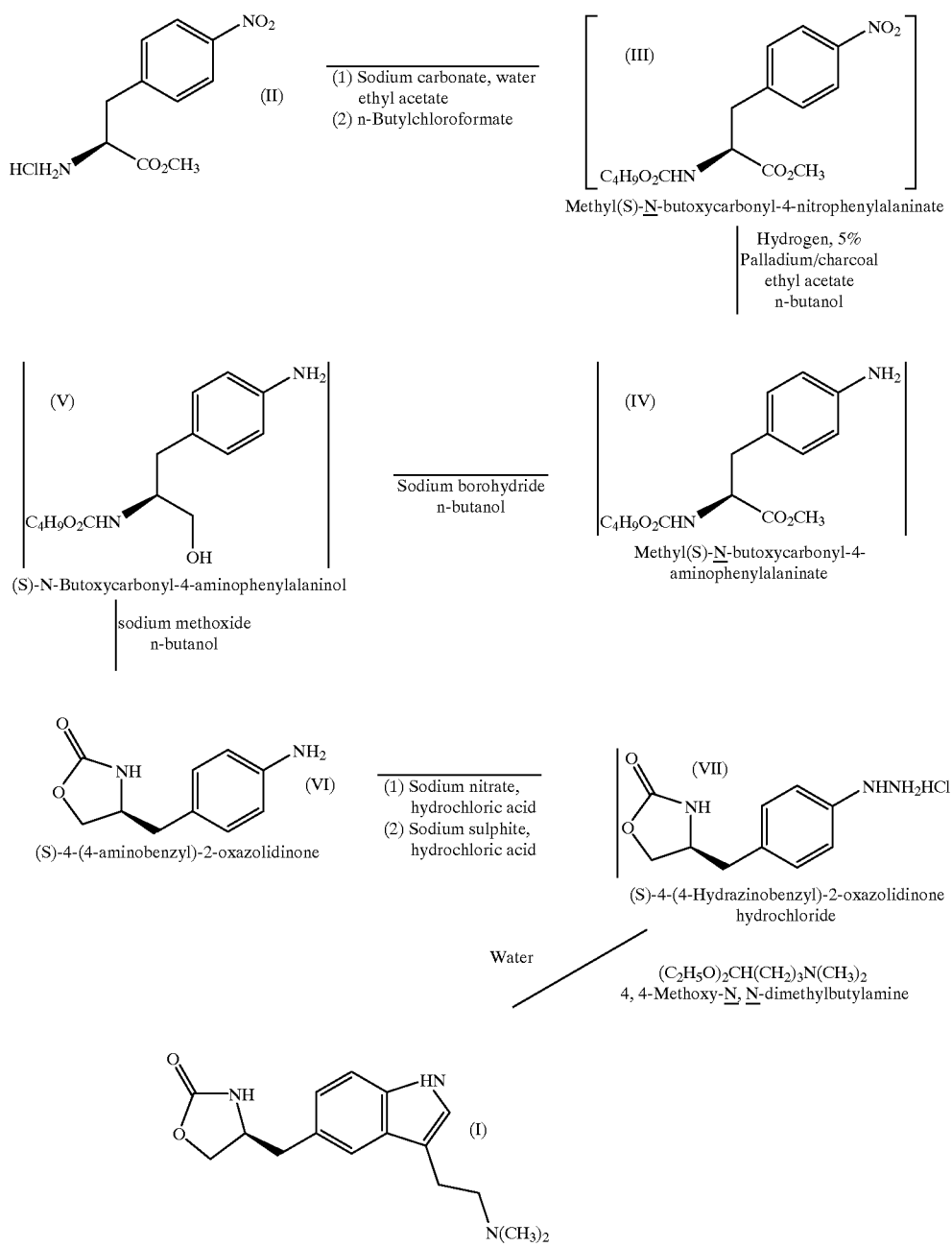

According to the second aspect of the present invention, there is provided a process for the purification of (S)-4-{[3-(dimethylamino)ethyl]-1H-indol-5-yl]-methyl}-2-oxazolidinone which process comprises the steps of a) dissolving crude (S)-4-{[3-(dimethylamino)ethyl]-1H-indol-5-yl]-methyl}-2-oxazolidinone in a refluxing mixture of ethanol in ethyl acetate and filtering the hot solution;

b) slowly cooling the filtered solution to a temperature about 5° C.

c) centrifuging the product from step b), washing with ethyl acetate then drying; and d) treating with acetone to remove solvated ethyl acetate.

Preferably the refluxing mixture is 10% ethanol in ethyl acetate. The hot solution is suitably decolourised using decolourising charcoal prior to filtration using filter aid.

The cooled filtered solution of step b) is suitably stirred over a prolonged period, which is preferably approximately 18 hours, prior to centrifugation.

The drying stage of step c) is preferably carried out under vacuum. Suitably the product is dried at an elevated non-extreme temperature, for example 40–60° C., which is preferably approximately 50° C.

The dried solid product of step c) is conveniently treated with a mixture of 20% acetone in water, at a non-extreme temperature, preferably 15–30° C., for example at room temperature. The resulting suspension is then cooled to a non-extreme reduced temperature, preferably about 5° C., and stirred. The product is then centrifuged, washed with ethyl acetate and dried, preferably under vacuum at a temperature of approximately 45° C.

The resulting product is a non-solvated solid of high purity.

In a third aspect, the present invention provides non-solvated, pure (S)-4-{[3-[2-dimethylamino)ethyl]-1-H-indol-5-yl]methyl}-2-oxalolidinone.

In further aspects, the invention provides compounds of formulae (III), (IV), (V) and (VI) as defined hereinbefore.

In still further aspects, the invention provides processes for preparing compounds of formulae (III), (IV), (V) and (VI) as follows:

Compound (III): process step a) of the first aspect of the invention and preferably as described on page 4;

Compound (IV): process step b) of the first aspect of the invention and preferably as described in the paragraph bridging pages 4 and 5;

Compound (V): process step c) of the first aspect of the invention and preferably as described on page 5; and Compound (VI): process step d) of the first aspect of the invention and preferably as described on page 5.

The invention will now be further described by the following examples.

EXAMPLE 1

A process for preparing (S)-4-[2-(dimethylamino) ethyl]-1H-indol-5-yl]methyl}-2-oxazolidinone in bulk.

STAGE 1: The preparation of methyl 4-nitro-(L)-phenylaninate hydrochloride

REACTION

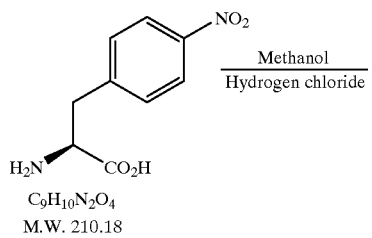

| MATERIALS | QUANTITY | MOLES |
|---|---|---|
| 4-Nitro-(L)-phenylanine | 100.0 kg | 475.8 |
| Methanol | 599.0 liters | |
| Hydrogen chloride | 45.3 kg | 1241.6 |
| Methanol (wash | 66.8 liters | |

PROCEDURE

Prepare a methanolic solution of hydrogen chloride by passing hydrogen chloride gas into a reactor containing methanol, maintaining temperature below 25° C. Charge to the reactor the 4-nitro-(L)-phenylanine and reflux for about 1 hour. Cool to about 0° C. and centrifuge the product (methyl 4-nitro-(L)-phenylalaninate hydrochloride). Wash the product with methanol and dry in vacuo at 50° C.

STAGE 2: The preparation of methyl (S)-N-butoxycarbonyl-4-nitrophenylalaninate

REACTION

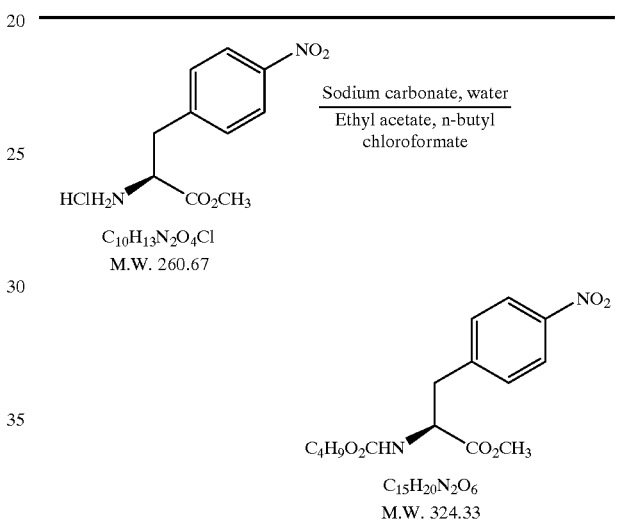

| MATERIALS | QUANTITY | MOLES |
|---|---|---|
| Methyl 4-nitro-(L)-phenylalaninate hydrochloride | 45.0 kg | 172.7 |
| Sodium carbonate | 20.1 kg | 189.6 |
| n-Butyl chloroformate | 24.0 kg | 175.8 |
| Ethyl acetate | 248.0 kg | |
| Water (demineralised) | 100.0 kg | |
| Water (wash) | 50.0 kg | |

PROCEDURE

Charge to the reactor demineralised water, methyl 4-nitro-(L)-phenylalaninate hydrochloride, sodium carbonate and ethyl acetate and cool the contents to about 20° C. with stirring. Add the n-butyl chloroformate to the reaction mixture whilst maintaining the temperature at about 30° C. and stir for about 30 minutes. Separate the aqueous layer and wash the ethyl acetate solution with water. The ethyl acetate solution of methyl (S)-N-butoxycarbonyl-4-nitrophenylalaninate is used directly at the next stage.

STAGE 3: The preparation of methyl (S)-N-butoxycarbonyl-4-aminophenylaninate

REACTION

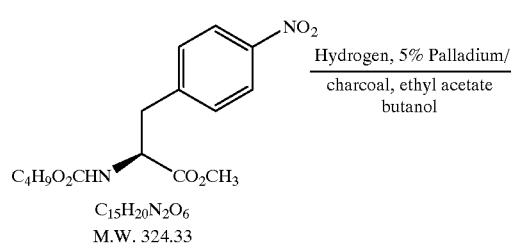

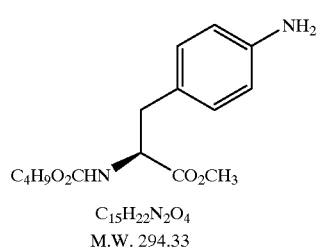

C₁₅H₂₂N₂O₄
M.W. 294.33

| MATERIALS | QUANTITY | MOLES |
| --- | --- | --- |
| Methyl (S)-N-butoxycarbonyl-4-nitrophenylalaninate | 56.0 kg | 172.7 |
| Ethyl acetate | 252.0 kg | |
| 5% Palladium charcoal (55% water wet) | 5.0 kg | |
| Ethyl acetate (filter wash) | 18.0 kg | |
| Sodium carbonate | 12.5 kg | |
| Water (demineralised) | 100.0 kg | |
| Filter aid | 3.5 kg | |
| Hydrogen | as required | |
| Butanol | 247.1 kg | |

PROCEDURE

Charge to the reactor the 5% palladium charcoal catalyst, the ethyl acetate solution of methyl (S)-N-butoxycarbonyl-4-nitrophenylalaninate and hydrogenate at about 20 psi of hydrogen, maintaining a temperature between 30° C. and 50° C. On completion, filter off the catalyst through filter aid and wash with ethyl acetate. Wash the ethyl acetate solution with aqueous sodium carbonate solution. The ethyl acetate solution of methyl (S)-N-butoxycarbonyl-4-aminophenylalaninate is partially distilled, butanol added and the mixture fractionated to remove the ethyl acetate. The butanol solution is used directly at the next stage.

STAGE 4: The preparation of (S)-N-butoxycarbonyl-4-aminophenylalaninol.

REACTION

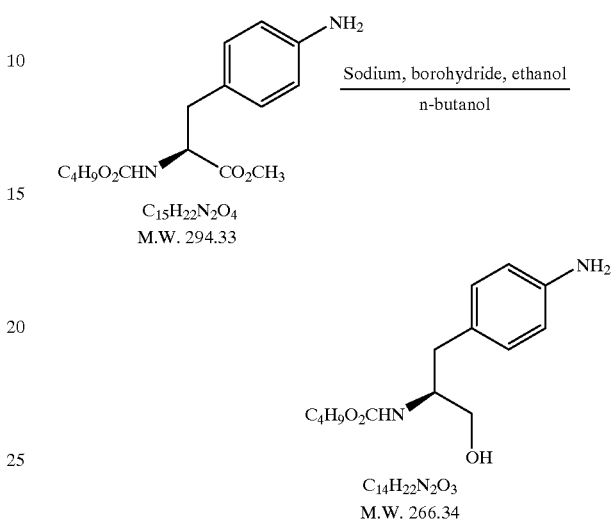

| MATERIALS | QUANTITY | MOLES |
| --- | --- | --- |
| Methyl (S)-N-butoxycarbonyl-4-aminophenylaminate | 50.8 kg | 172.8 |
| n-Butanol | 305 liters | |
| Sodium borohydride (total) | 6.5 kg | 172.8 |
| conc. Hydrochloric acid | 20.2 liters | 300 |
| Water (demineralised - for dilution of acid) | 20.2 kg | |
| Water (demineralised) | 150.0 kg | |
| conc. Ammonia solution (d = 0.88) | 14.6 liters | |

PROCEDURE

Charge to the reactor the butanol solution of methyl (S)-N-butoxycarbonyl-4-aminophenylalaninate from Stage 3, and dilute with n-butanol to the required volume. Cool the reactor contents to about 25° C. Under a nitrogen atmosphere add half the amount of sodium borohydride whilst maintaining a reaction temperature of about 25° C. Stir for 3 hours and then add the second half of sodium borohydride. Further stir the mixture for 5 hours and warm to 35° C. After this time stir the reaction mixture for about 12 hours and then slowly add aqueous hydrochloric acid, maintaining temperature at about 30° C, to decompose any excess sodium borohydride. Add water, warm to about 35° C. and add ammonia solution to adjust to approximately pH10. Separate the aqueous layer and whilst maintaining a temperature of about 35° C., wash the organic layer with water. Distil some of the butanol, whilst simultaneously azeotroping dry the solution. The dry butanol solution is used directly at the next stage.

STAGE 5: The preparation of (S)-4-(4-aminobenzyl)-2-oxazolidinone.

REACTION

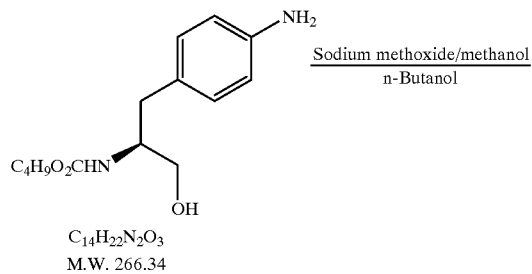

C₁₄H₂₂N₂O₃
M.W. 266.34

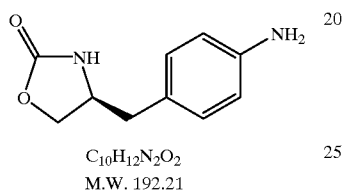

C₁₀H₁₂N₂O₂
M.W. 192.21

| MATERIALS | QUANTITY | MOLES |
|---|---|---|
| (S)-N-Butoxycarbonyl-4-aminophenylalaninol | 91.9 kg | 345.0 |
| n-Butanol | 260.0 liters | |
| Sodium methoxide (30% weight in methanol solution) | 7.5 kg | 4.7 |
| Charcoal | 2.0 kg | |
| n-Butanol (filter wash) | 20.0 kg | |
| n-Butanol (product wash) | 30.0 kg | |
| Filter aid | 2.0 kg | |

PROCEDURE

Charge to the reactor the dry solution of (S)-N-butoxycarbonyl-4-aminophenylalaninol in n-butanol from Stage 4 and add decolourising charcoal. Treat the dry solution at about 85° C. with the slow addition of sodium methoxide in methanol. Heat the reaction mixture at 85° C. with the slow addition of sodium methoxide in methanol. Heat the reaction mixture at 85° C. for a further 30 minutes and then filter hot through filter aid. After cooling the solution at 5–10° C. for at least 8 hours, centrifuge the mixture, wash the filtered product with n-butanol and dry at about 50° C. in vacuo.

STAGE 6A: The preparation of (S)-4-{3-[2-(dimethylamino)ethyl]-1H-indol-5-yl]methyl}-2-oxazolidinone.

REACTION

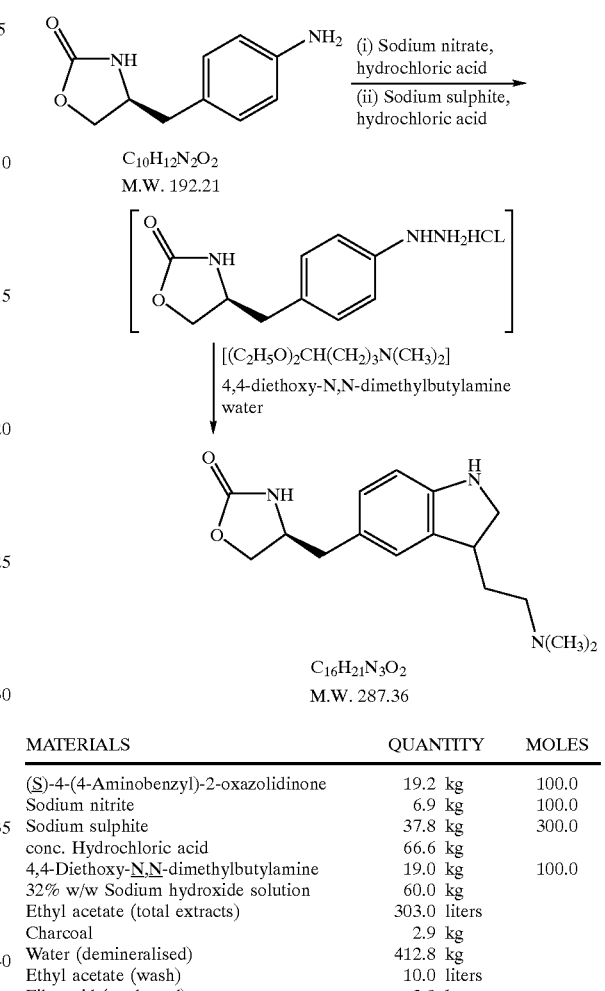

| MATERIALS | QUANTITY | MOLES |
|---|---|---|
| (S)-4-(4-Aminobenzyl)-2-oxazolidinone | 19.2 kg | 100.0 |
| Sodium nitrite | 6.9 kg | 100.0 |
| Sodium sulphite | 37.8 kg | 300.0 |
| conc. Hydrochloric acid | 66.6 kg | |
| 4,4-Diethoxy-N,N-dimethylbutylamine | 19.0 kg | 100.0 |
| 32% w/w Sodium hydroxide solution | 60.0 kg | |
| Ethyl acetate (total extracts) | 303.0 liters | |
| Charcoal | 2.9 kg | |
| Water (demineralised) | 412.8 kg | |
| Ethyl acetate (wash) | 10.0 liters | |
| Filter aid (total used) | 2.0 kg | |

PROCEDURE

Charge to the reactor conc. hydrochloric acid, demineralised water and (S)-4-(4-aminobenzyl)-2-oxazolidinone. Cool the reactor contents to between 0–5° C. and add aqueous sodium nitrite solution, maintaining the temperature below 5° C. After stirring for about 30 minutes add the diazonium salt solution to a chilled aqueous solution of sodium sulphite, maintaining the temperature below 10° C. After stirring for 15 minutes slowly heat the resulting mixture to about 55–60° C., and then slowly add hydrochloric acid. The solution is maintained at about 60° C. for about 18 hours.

Dilute the reaction mixture with water and heat to about 90° C. Under a nitrogen atmosphere slowly add 4,4-diethoxy-N,N-dimethylbutylamine and heat at reflux for about 3 hours. Cool, and adjust the mixture to about pH7 using sodium hydroxide solution. Extract with ethyl acetate and then adjust the aqueous layer to about pH10, again using sodium hydroxide solution. Extract the product at about 50° C. using ethyl acetate. Treat the combined ethyl acetate extracts (containing the product) with decolourising charcoal, and filter through filter aid. Distil off most of the solvent and chill the suspension to about 5° C. Centrifuge the crude product, wash with ethyl acetate and vacuum dry at 50° C.

STAGE 6B: Purification of (S)-4-{3-[2-(dimethylamino) ethyl]-1H-indol-5-yl]methyl}-2-oxazolidinone

| MATERIALS | QUANTITY |
|---|---|
| Ethyl acetate | 109.4 liters |
| Ethanol | 12.3 liters |
| Charcoal | 2.4 kg |
| Ethyl acetate (product wash) | 5.0 liters |
| Acetone | 11.8 liters |
| Water (demineralised) | 47.3 kg |
| Water (demineralised) (product wash) | 10.0 kg |
| Filter acid | 2.0 kg |

The crude product of step 6A is dissolved in a refluxing mixture of 10% ethanol in ethyl acetate, treated with decolourising charcoal and filtered hot through filter aid. The solution is slowly cooled to above 5° C. and stirred for 18 hours. The purified product is then centrifuged, washed with ethyl acetate and vacuum dried at 50° C. In order to remove solvated ethyl acetate, the dry solid is added to a mixture of 20% acetone in water at ambient temperature and stirred for 1 hour. The suspension is cooled to about 5° C. for about 1 hour before centrifuging the product, washing with ethyl acetate and drying in vacuo at about 45° C.

EXAMPLE 2

Alternative, preparation of Methyl (S)-N-butoxycarbonyl-4-nitrophenylalaninate (Compound of formula (III))

A mixture of methyl-4-nitro-(L)-phenylalaninate hydrochloride (40.00 g, 0.153 mole) and sodium hydrogen carbonate (73 g, 0.870 mole) in 1,4-dioxane (1000 ml) was stirred at approximately 10° C. under anhydrous conditions. A solution of butyl chloroformate (23.12 g, 21.52 ml, 0.169 mole) in 1,4-dioxane (200 ml) was added over a period of ten minutes (reaction temperature approximately 13° C.). The resulting suspension was allowed to warm to room temperature and stirred for three hours. The reaction was quenched slowly into water (1600 ml) and then extracted with ethyl acetate (3×650 ml). The combined ethyl acetate extracts were washed with brine (1000 ml), dried over anhydrous magnesium sulphate, filtered and evaporated to an oil. Residual solvent was removed using an oil pump at 50° C. to afford a syrup (51.34 g, 103% yield) which gradually solidified on standing.

TLC[$SiO_2$,EtOAc] was homogeneous ($R_f$=0.59).

$^1$H NMR (60 MHz, CDCl$_3$) was consistent with structure of carbamate.

EXAMPLE 3

Alternative preparation of Methyl (S)-N-butoxycarbonyl-4-aminophenylalaninate (Compound of formula (IV))

A solution of the compound prepared by Example 2 [45.00 g, 0.139 mole] in ethanol (845 ml) was added to moist 10% palladium on carbon (Type 87L, 61.1% H$_2$O) [~4.5 g] under an atmosphere of nitrogen. The reaction was set up for hydrogenation at room temperature under normal atmospheric pressure. There was a steady uptake of hydrogen (~9700 ml) over nine hours. The catalyst was filtered off on hyflo and washed with ethanol (100 ml). The filtrate was concentrated in vacuo (water bath temp. <40° C.) and the last traces of solvent removed using an oil pump to afford a brown gum (41.70 g, 101%).

TLC [$SiO_2$, EtOAc] showed the required product ($R_f$= 0.49) with traces of a faster running impurity.

$^1$H NMR (300 MHz, CDCl$_3$) was consistent with structure of product and residual ethanol.

EXAMPLE 4

Alternative preparation of (S)-N-Butoxycarbonyl-4-aminophenylalaninol (Compound of formula (V)).

To a stirred suspension of sodium borohydride (14.80 g, 0.390 mole) in SVM (150 ml), was added dropwise a solution of the compound prepared by Example 3 [76.40 g, 0.260 mole) in SVM (460 ml) at room temperature. The reaction was left stirring overnight (~18 hours) after which TLC (SiO$_2$, EtOAc) indicated complete consumption of starting material. The reaction mixture was acidified to ~pH4 with 2M aqueous hydrochloric acid with ice-cooling to a temperature of approximately 10° C. The resulting mixture was concentrated to a solid residue and saturated aqueous sodium hydrogen carbonate (2000 ml) was added slowly. The aqueous mixture (pH~8) was extracted with ethyl acetate (2×750 ml) and the combined organic extracts dried (magnesium sulphate), filtered and concentrated to a pale pink waxy sold (64.56 g, 93% yield).

TLC [SiO$_2$, EtOAc] indicated the required product ($R_f$= 0.33) with traces of impurities.

$^1$H No (60 MHz, CDCl$_3$) was consistent with structure of alaninol.

I claim:

1. A process for the preparation of a (S)-4-{[3-[2 (dimethylamino)ethyl]-1H-indol-5-yl]methyl}-2-oxazolidinone represented by formula (I)

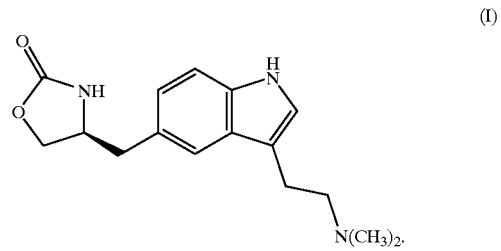

(I)

which process comprises the steps of
a) forming a carbamate from methyl 4-nitro-(L)-phenylalaninate hydrochloride, represented by formula (II)

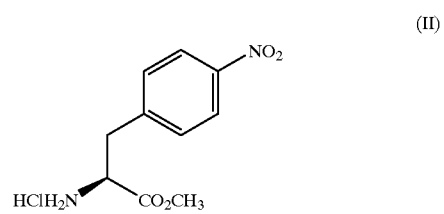

(II)

by adding sodium carbonate or sodium hydrogen carbonate and n-butyl chloroformate and reacting to give methyl(S)-N-butoxycarbonyl-4-nitrophenylalaninate, represented by formula (III)

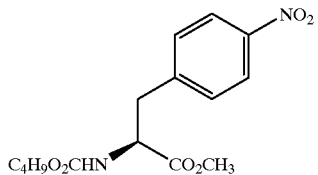

(III)

b) reducing the compound of formula (III) to give methyl (S)-N-butoxycarbonyl-4-amino phenylalaninate, represented by formula (IV)

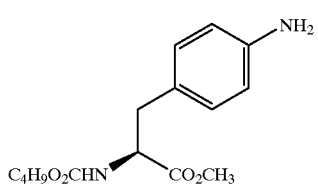

(IV)

c) reducing the methyl ester grouping —$CO_2CH_3$ in the compound of formula (IV) to give (S)-N-butoxycarbonyl-4-aminophenylalaninol, represented by formula (V)

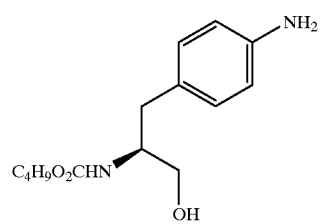

(V)

d) a ring closure of the compound of formula (V) without the need for phosgene to give (S)-4-(4-aminobenzyl)-2-oxazolidinone, represented by formula (VI)

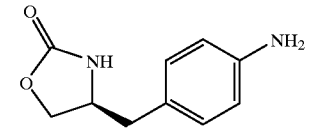

(VI)

e) preparation of the diazonium salt of the compound of formula (VI) followed by reduction without the need for tin chloride to give the hydrazine (S)-4-(4-hydrazinobenzyl)-2-oxazolidinone hydrochloride, represented by formula (VII)

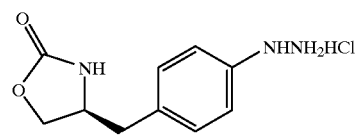

(VII)

f) Fischer reaction of the compound of formula (VII) to give the compound of formula (I).

2. A process according to claim 1 wherein one or more of steps a) to f) are carried out using a one pot procedure.

3. A process according to claim 1 or 2 wherein steps a) to d) are carried out by a one pot procedure followed by isolation of the compound of formula (VI) and then a second one pot procedure for steps e) and f).

4. A process according to claim 1 or 2, wherein step b) is carried out by hydrogenation.

5. A process according to claim 1 or 2, wherein the step c) reduction is effected using sodium borohydride.

6. A process according to claim 1 or 2, wherein step d) is carried out on a dry butanol solution of the compound of formula (V).

7. A process according to claim 1 or 2, wherein the ring closure is carried out using a 30% solution of sodium methoxide in methanol at a temperature which is in the range of 50–120° C.

8. A process according to claim 1 or 2, wherein step e) is carried out by
(I) reacting the compound of formula (VI) with sodium nitrite, and
(ii) reducing the diazonium salt formed in (i) using sodium sulphite.

9. A process according to claim 1 or 2, wherein the Fischer reaction of step (f) is carried out at a relatively high dilution.

10. A process according to claim 3, wherein step a) is carried out in the presence of an aqueous ethyl acetate solvent, using sodium carbonate.

11. A process according to claim 10, wherein the addition of sodium carbonate in step (a) takes place at a temperature of approximately 20° C. and the addition of N-butyl chloroformate takes place at a temperature of approximately 30° C.

12. A process for the preparation of a (S)-4-{[3-[2(dimethylamino)ethyl]-1H-indol-5-yl]methyl}-2-oxazolidinone, represented by formula (I)

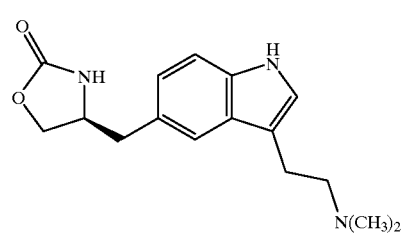

(I)

which process comprises the steps of
a) forming a carbamate from methyl 4-nitro-(L)-phenylalaninate hydrochloride, represented by formula (II)

(II)

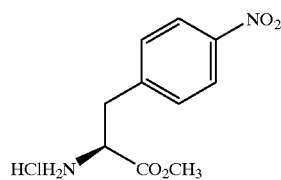

by adding sodium carbonate and n-butyl chloroformate in the presence of an aqueous ethyl acetate solvent and reacting to give methyl(S)-N-butoxycarbonyl-4-nitrophenylalaninate, represented by formula (III)

(III)

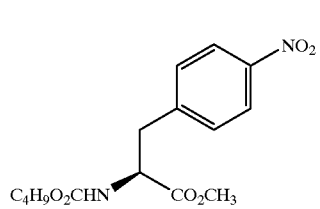

b) reducing the compound of formula (III) to give methyl (S)-N-butoxycarbonyl-4-amino phenylalaninate, represented by formula (IV)

(IV)

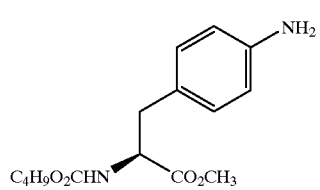

c) reducing the methyl ester grouping —$CO_2CH_3$ in the compound of formula (IV) to give (S)-N-butoxycarbonyl-4-aminophenylalaninol, represented by formula (V)

(V)

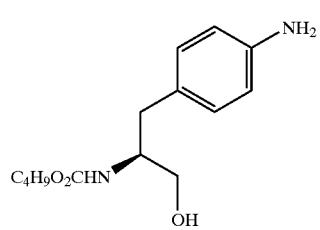

d) a ring closure of the compound of formula (V) withoutt the need for phosgene to give (S)-4-(4-aminobenzyl)-2-oxazolidinone, represented by formula (VI)

(VI)

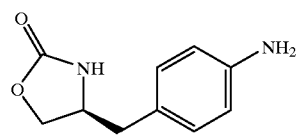

e) preparation of the diazonium salt of the compound of formula (VI) followed by reduction without the need for tin chloride to give the hydrazine (S)-4-(4-hydrazinobenzyl)-2-oxazolidinone hydrochloride, represented by formula (VII)

(VII)

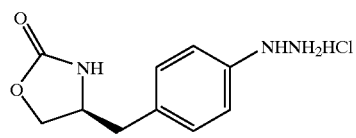

f) Fischer reaction of the compound of formula (VII) to give the compound of formula (I).

13. A process according to claim 12, wherein one or more of steps a) to f) are carried out using a one pot procedure.

14. A process according to claim 12 or 13, wherein steps a) to d) are carried out by a first one pot procedure followed by isolation of the compound of formula (VI) and then a second one pot procedure for steps e) and f).

15. A process according to claim 12 or 13, wherein the addition of sodium carbonate in step a) takes place at a temperature of approximately 20° C. and the addition of N-butyl chloroformate takes place at a temperature of approximately 30° C.

16. A process according to claim 12 or 13, wherein the step c) reduction is effected using sodium borohydride.

17. A process according to claim 12 or 13, wherein step d) is carried out on a dry butanol solution of the compound of formula (V).

18. A process according to claim 12 or 13, wherein the ring closure of step d) is carried out using a 30% solution of sodium methoxide in methanol at a temperature which is in the range of 50–120° C.

19. A process according to claim 12 or 13, wherein step e) is carried out by
   (i) reacting the compound of formula (VI) with sodium nitrite, and
   (ii) reducing the diazonium salt formed in (i) using sodium sulphite.

20. A process according to claim 12 or 13, wherein the Fischer reaction of step f) is carried out at a relatively high dilution.

* * * * *